US010094833B2

(12) United States Patent
Taggart et al.

(10) Patent No.: US 10,094,833 B2
(45) Date of Patent: Oct. 9, 2018

(54) METHOD AND KIT FOR DETECTING BACTERIAL INFECTION

(71) Applicant: Randox Laboratories Limited, Crumlin (GB)

(72) Inventors: Clifford Taggart, Belfast (GB); Sinead Weldon, Belfast (GB); Chris Scott, Belfast (GB)

(73) Assignee: Randox Laboratories Limited, Crumlin (GB)

( * ) Notice: Subject to any disclaimer, the term of this patent is extended or adjusted under 35 U.S.C. 154(b) by 0 days.

(21) Appl. No.: 15/502,711

(22) PCT Filed: Aug. 6, 2015

(86) PCT No.: PCT/EP2015/068209
§ 371 (c)(1),
(2) Date: Feb. 8, 2017

(87) PCT Pub. No.: WO2016/020503
PCT Pub. Date: Feb. 11, 2016

(65) Prior Publication Data
US 2017/0212117 A1 Jul. 27, 2017

(30) Foreign Application Priority Data

Aug. 8, 2014 (GB) .................................. 1414079.2
Jun. 2, 2015 (GB) .................................. 1509564.9

(51) Int. Cl.
*A61K 39/00* (2006.01)
*A61K 45/00* (2006.01)
*A61K 39/02* (2006.01)
*G01N 33/573* (2006.01)
*C07K 5/113* (2006.01)
*C07K 16/40* (2006.01)

(52) U.S. Cl.
CPC ......... *G01N 33/573* (2013.01); *C07K 5/1021* (2013.01); *C07K 16/40* (2013.01); *C07K 2317/34* (2013.01); *G01N 2333/96425* (2013.01); *G01N 2800/26* (2013.01)

(58) Field of Classification Search
CPC ........ A61K 38/04; A61K 38/17; A61K 39/00; A61K 39/395
USPC ..... 424/9.1, 9.2, 130.1, 139.1, 184.1, 185.1, 424/234.1, 278.1
See application file for complete search history.

(56) References Cited

U.S. PATENT DOCUMENTS

| 6,869,925 | B1 | 3/2005 | Eisenberg et al. | |
|---|---|---|---|---|
| 7,582,734 | B2 * | 9/2009 | Wittamer | C07K 14/475 530/387.1 |
| 2007/0166779 | A1 | 7/2007 | Belkowski et al. | |
| 2008/0227125 | A1 * | 9/2008 | Argoud-Puy | C07K 14/47 435/7.92 |
| 2009/0004648 | A1 * | 1/2009 | Cojocaru | C12Q 1/6886 435/6.12 |
| 2009/0275068 | A1 * | 11/2009 | Belkowski | C12Q 1/37 435/23 |

FOREIGN PATENT DOCUMENTS

| JP | 7-103977 A | 4/1995 |
|---|---|---|
| WO | 02/095411 A1 | 11/2002 |
| WO | 2005/047328 A2 | 5/2005 |
| WO | 2009/045508 A1 | 4/2009 |

OTHER PUBLICATIONS

International Search Report and Written Opinion for corresponding PCT Application No. PCT/EP2015/068209.
Kida et al.; Serum Secretory Leukoprotease Inhibitor Levels to Diagnose Pneumonia in the Elderly; Foundations in Microbiology, vol. 146, No. 6, Jan. 1, 1992, pp. 1426-1429.
Posnett et al.; A Novel Method for Producing Anti-peptide Antibodies Production of Site-Specific Antibodies to the T Cell Antigen Receptor Beta-Chain; The Journal of Biological Chemistry by The American Society for Biochemistry and Molecular Biology, vol. 263, No. 4, Feb. 5, 1988, pp. 1719-1725.
Twigg et al.; Development of New Antibodies for the Specific Detection of Cleaved SLPI to Facilitate More Rapid Testing of Bacterial Infection Status in Chronic Lung Disease; AACC 2015 Annual Meeting and Clinical Lab Expo, Jul. 29, 2015.
Water et al.; Ultrastructural Localization of Bronchial Antileukoprotease in Central and Peripheral Human Airways by a Gold-Labeling Technique Using Monoclonal Antibodies; The American Review of Respiratory Disease, American Thoracic Society, vol. 133, No. 5, Jan. 1, 1986, pp. 882-890.
Weldon et al.; Decreased Levels of Secretory Leukoprotease Inhibitor in the Pseudomonas-Infected Cystic Fibrosis Lung Are Due to Neutrophil Elastase Degradation; The Journal of Immunology, vol. 183, No. 12, Dec. 15, 2009, pp. 8148-8156.

\* cited by examiner

*Primary Examiner* — Rodney P Swartz
(74) *Attorney, Agent, or Firm* — Gavrilovich, Dodd & Lindsey, LLP

(57) ABSTRACT

The invention relates to a novel antibody which binds to C-SLPI selected from the group consisting of SEQ ID NOs: 3 and 4.

Figure 1:
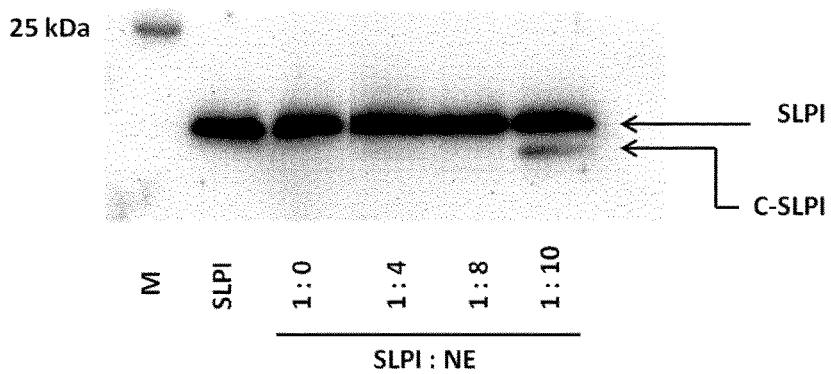

3 Claims, 9 Drawing Sheets
Specification includes a Sequence Listing.

| | |
|---|---|
| Parameter | NE (AAPV-AMC) |
| Number of XY Pairs | 12 |
| Spearman r | 0.5438 |
| 95% confidence interval | -0.06313 to 0.8571 |
| P value (two-tailed) | 0.0676 |
| P value summary | ns |
| Exact or approximate P value? | Exact |

Figure 5.

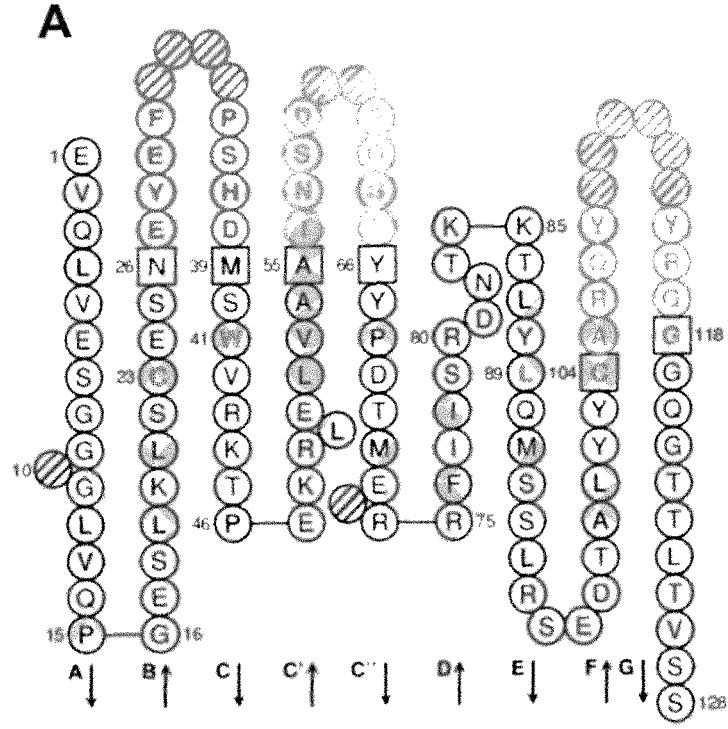
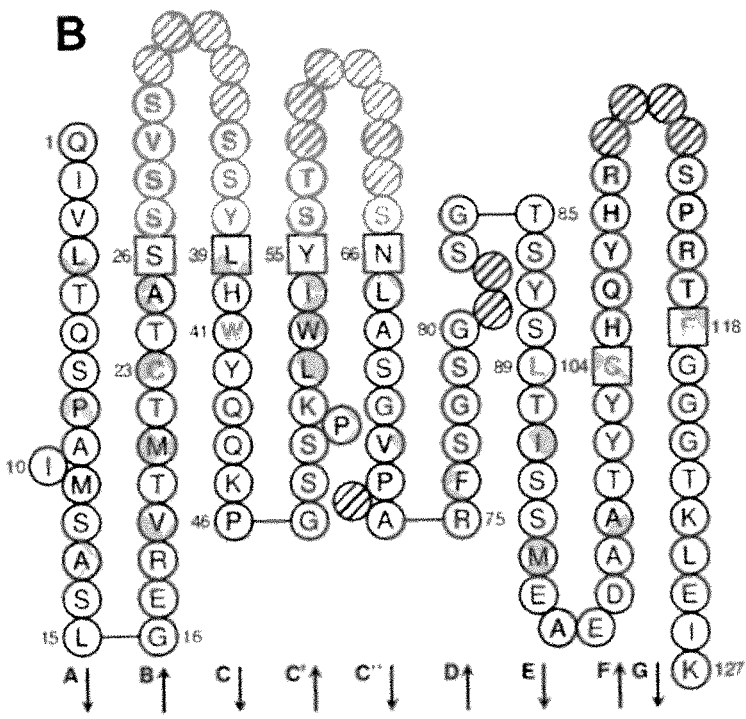
Figure 8

$V_H$

CLUSTAL 2.1 multiple sequence alignment

```
C4.8VH      EVQLVESGGGLVQPGESLKLSCESNEYEFPSHDMSWVRKTPEKRLELVAAINSDGG--ST 58
C5.5VH      EVQLVESGGGLVHPQGSLKLSCTASGFTFNTYDMNWVRQAPGKGLEWVARIRTKSYYYAT 60
            ************:*  ******  :.  : *  ::**.***::* * ** ** *.:..    :*

C4.8VH      YYPDTMERRFIISRDNTKKTLYLQMSSLRSEDTALYYCARQYYRGG-----GQGTTLTVS 113
C5.5VH      YYADSVKDRFTISRDDSQTMLYLQLNNLKTEDTALYYCVRRSGNYGAMDYWGQGTSVTVS 120
            **.*:::  ** ****:::.  ****:..*::*********.*:   .  *      ****::***

C4.8VH      S 114
C5.5VH      S 121
            *
```

$V_L$

```
C4.8VL      QIVLTQSPAIMSASLGERVTMTCTASSSVSSSYLHWYQQKPGSSPKLWIYSTSNLASGVP 60
C5.5VL      QIVLTQSPAIMSASLGERVTMTCTASSSVSSSYLHWYQQKPGSSPKLWIYSTSNLASGVP 60
            ************************************************************

C4.8VL      ARFSGSGSGTSYSLTISSMEAEDAATYYCHQYHRSPRTFGGGTKLEIK 108
C5.5VL      ARFSGSGSGTSYSLTISSMEAEDAATYYCHQYHRSPRTFGGGTKLEIK 108
            ************************************************
```

Figure 10.

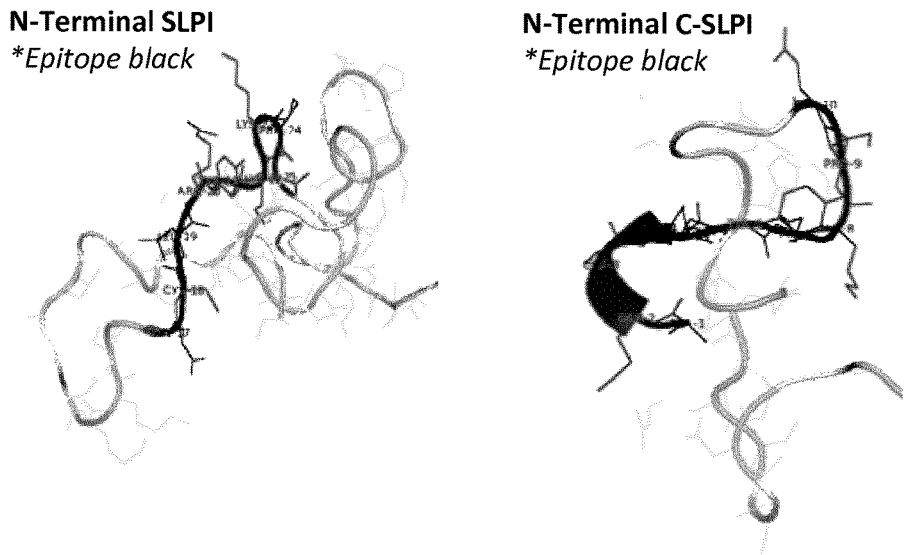

Figure 11.

METHOD AND KIT FOR DETECTING BACTERIAL INFECTION

RELATED APPLICATIONS

The present application is a U.S. National Stage patent application under 35 USC 371, claiming priority to PCT Application Serial No. PCT/EP2015/068209, filed on Aug. 6, 2015; which claims priority to GB 1414079.2, filed Aug. 8, 2014 and GB 1509564.9, filed Jun. 2, 2015, the entirety of all of which are incorporated herein by reference.

FIELD OF THE INVENTION

The present invention relates to detecting C-SLPI, a C-terminal fragment of SLPI (Secretory leukocyte protease inhibitor). Specifically, the invention describes novel immunogens, novel antibodies, kits and methods for detecting C-SLPI and their use in disease research, diagnosis and treatment.

BACKGROUND

Chronic lung diseases such as Cystic Fibrosis (CF) and Chronic Obstructive Pulmonary Disease (COPD) are often associated with chronic bacterial infection (Gibson et al. 2013). This chronic bacterial infection is due to these patients having a highly compromised innate immune system that prevents the body from clearing infections from the lung, in turn leading to an increased, detrimental inflammatory response and remodelling of the lung tissue (Voynow et al. 2008). One such bacterium that is linked with chronic infection in both CF and COPD patients is *Pseudomonas aeruginosa*; once established, this bacterium is almost impossible for the patient to eradicate (Murray et al. 2007). The presence of *P. aeruginosa* and other bacterial pathogens such as *Staphylococcus aureus* and *Burkholderia* sp. in these patients has the effect of recruiting a high number of neutrophils to the sites of infection within the lung and, as such, increases the local concentration of the protease, neutrophil elastase (NE) (Voynow et al. 2008). This high level of NE overwhelms the body's natural defence to proteases—the antiprotease screen (Voynow et al. 2008). One such antiprotease that is affected by high levels of NE is human Secretory leukocyte protease inhibitor (SLPI).

Mature SLPI is an 11.7 kDa (107-amino acid) antiprotease of SEQ ID NO: 2 that is produced by a number of immune and epithelial cells and can be found in multiple areas of the body including the lungs (Seemüller et al. 1986; Voynow et al. 2008). The production of mature SLPI (from SLPI of SEQ ID NO: 1 that includes, at its N-terminus, a 25 residue signal peptide [UniProtKB/Swiss-Prot-P03973]) is triggered by a number of different factors including the presence of the bacterial endotoxin lipopolysaccharide (LPS), protease production and the presence of differing cytokines (Kammouni et al. 1997). In general, the role of mature SLPI is to protect the body's tissues from the detrimental effects of differing proteases. However, mature SLPI also has anti-bacterial and anti-viral properties (Doumas & Kolokotronis 2005; Hiemstra et al. 1996). Findings by Weldon et al. (2009) have shown that, when CF patients are chronically infected with *P. aeruginosa*, the associated increased level of NE has the effect of cleaving SLPI at two sites within the polypeptide, Ser15-Ala16 and Ala16-Gln17 (Weldon et al. 2009), resulting in two species of C-terminal polypeptide fragments:

Species 1 ($Q^{17}$-$A^{107}$) (10,152 Da)—Weldon et al. 2009 (SEQ ID NO: 3)

QCLRYKKPECQSDWQCPGKKRCCPDTCGIKCLDPVDTPNPTRRKPGKCP
VTYGQCLMLNPPNFCEMDGQCKRDLKCCMGMCGKSCVSPVKA

Species 2 ($A^{16}$-$A^{107}$) (10,223 Da)—Weldon et al. 2009 (SEQ ID NO: 4)

AQCLRYKKPECQSDWQCPGKKRCCPDTCGIKCLDPVDTPNPTRRKPGK
CPVTYGQCLMLNPPNFCEMDGQCKRDLKCCMGMCGKSCVSPVKA.

The term "C-SLPI" as used herein, describes species 1 and 2 above (SEQ ID NOs: 3 and 4) that are each the C-terminal cleavage product of mature SLPI, cleaved by NE, each of which having significantly reduced biological activity in comparison with full length mature SLPI (Weldon et al. 2009).

Weldon et al. 2009 identified C-SLPI of SEQ ID NOs: 3 or 4 as being a potential biomarker for bacterial infection in, for example, CF patients. As such, C-SLPI of SEQ ID NOs: 3 or 4 have the potential for commercial exploitation as a test for bacterial infection. The aim of this test would be to improve on the current laborious and time-consuming classical microbiological diagnostic approach. The advantage of this would be to speed up diagnosis, so that treatment could be initiated more expediently and, therefore, reduce the lung pathology associated with bacterial infection.

The inventors describe herein antibodies with a unique specificity for C-SLPI of SEQ ID NOs: 3 or 4.

SUMMARY OF THE INVENTION

The invention describes novel antibodies, monoclonal antibodies, specific for C-SLPI of SEQ ID NOs: 3 or 4 that enable kits and immunoassay methods for the detection and determination of C-SLPI of SEQ ID NOs: 3 or 4. The immunoassays have application, for example, in detecting, determining or monitoring bacterial infection. The invention is underpinned by a novel immunogen comprising a hapten of SEQ ID NO: 5 useful for the production of said antibodies.

DRAWINGS

FIG. 1. Western blot showing SLPI cleavage by NE. In order to establish an optimal incubation protocol for the production of C-SLPI, recombinant SLPI was incubated with varying molar ratios of NE for 16 h at 37° C. in an appropriate buffer. Successful cleavage of SLPI was observed at molar ratios of 1:4, 1:8 and 1:10 SLPI to NE.

Figure 2:
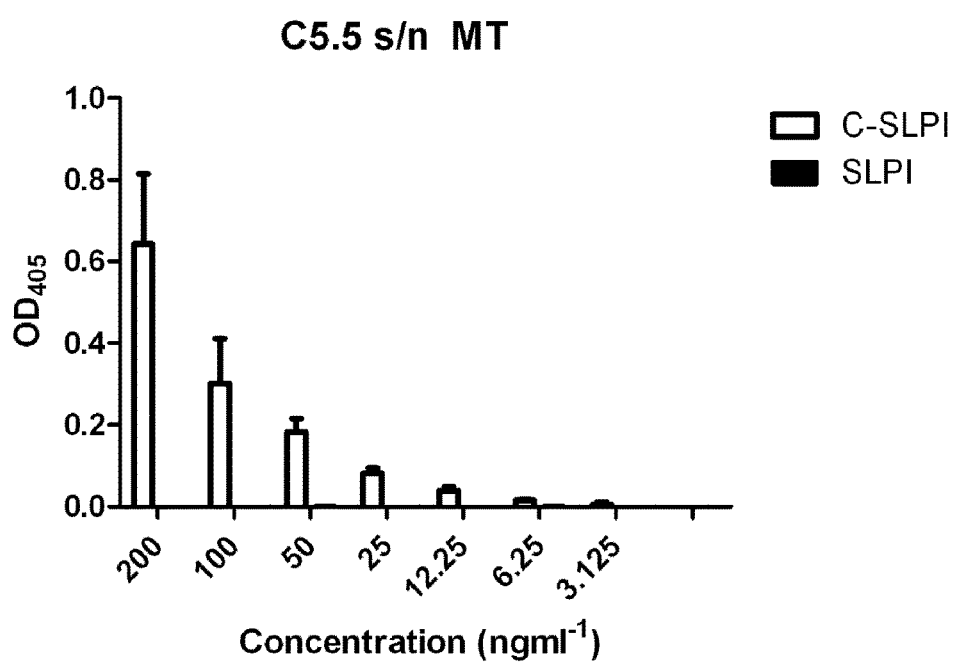

FIG. 2. C-SLPI hybridoma supernatant testing against known concentrations of C-SLPI and SLPI. Supernatant from C5.5 was tested for activity against known concentrations of both C-SLPI (white bars) and SLPI (black bars) in an ELISA assay. Supernatant from C5.5 recognised C-SLPI in a concentration-dependent manner and showed no cross reaction with SLPI.

Figure 3:
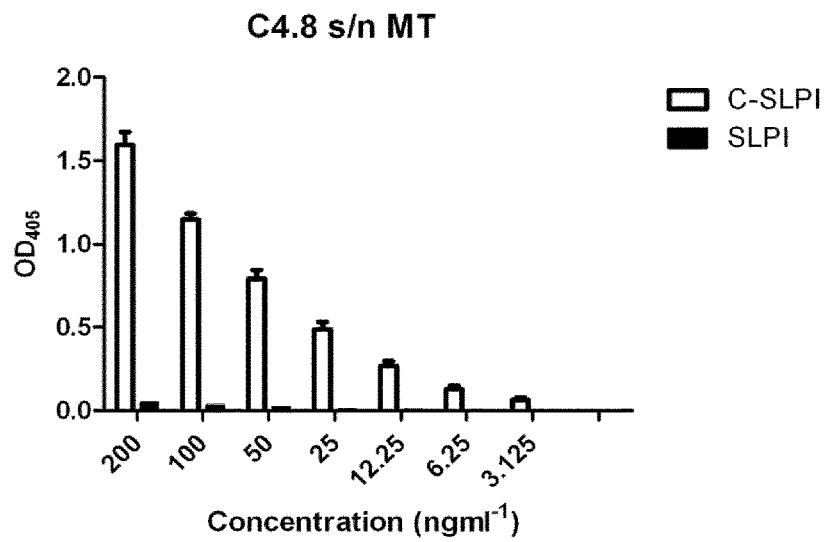

FIG. 3. C-SLPI hybridoma supernatant testing against known concentrations of C-SLPI and SLPI. Supernatant from C4.8 was tested for activity against known concentrations of both C-SLPI (white bars) and SLPI (black bars) in an ELISA assay. Supernatant from C4.8 recognised C-SLPI in a concentration-dependent manner and showed negligible cross reaction with SLPI.

Figure 4:
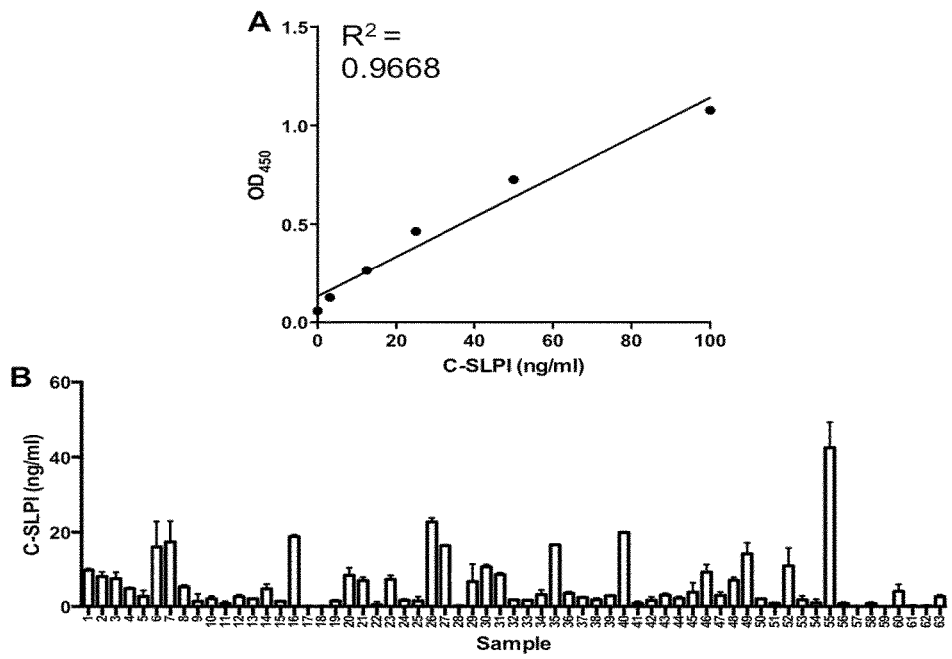

FIG. 4. Detection of C-SLPI in CF sputum samples. CF sputum samples were assayed via ELISA for the presence of C-SLPI using the supernatant from hybridoma clone C5.5 as a capture antibody. Standard curve generated by assaying known concentration of C-SLPI produced by incubation of recombinant SLPI with NE (A). C-SLPI concentrations in 63 sputum samples derived from CF patients as identified via ELISA using C5.5 as a capture antibody (B).

FIG. 5. Correlation of C-SLPI concentration in CF with NE activity. CF sputum samples were assayed for NE activity using substrate MeOSuc-AAPV-AMC and the results correlated with C-SLPI concentrations found in each sample as identified via ELISA using C5.5 supernatant. Although no direct correlation between C-SLPI concentration and NE activity was observed, the p value was close to significance (p=0.0676).

Figure 6:
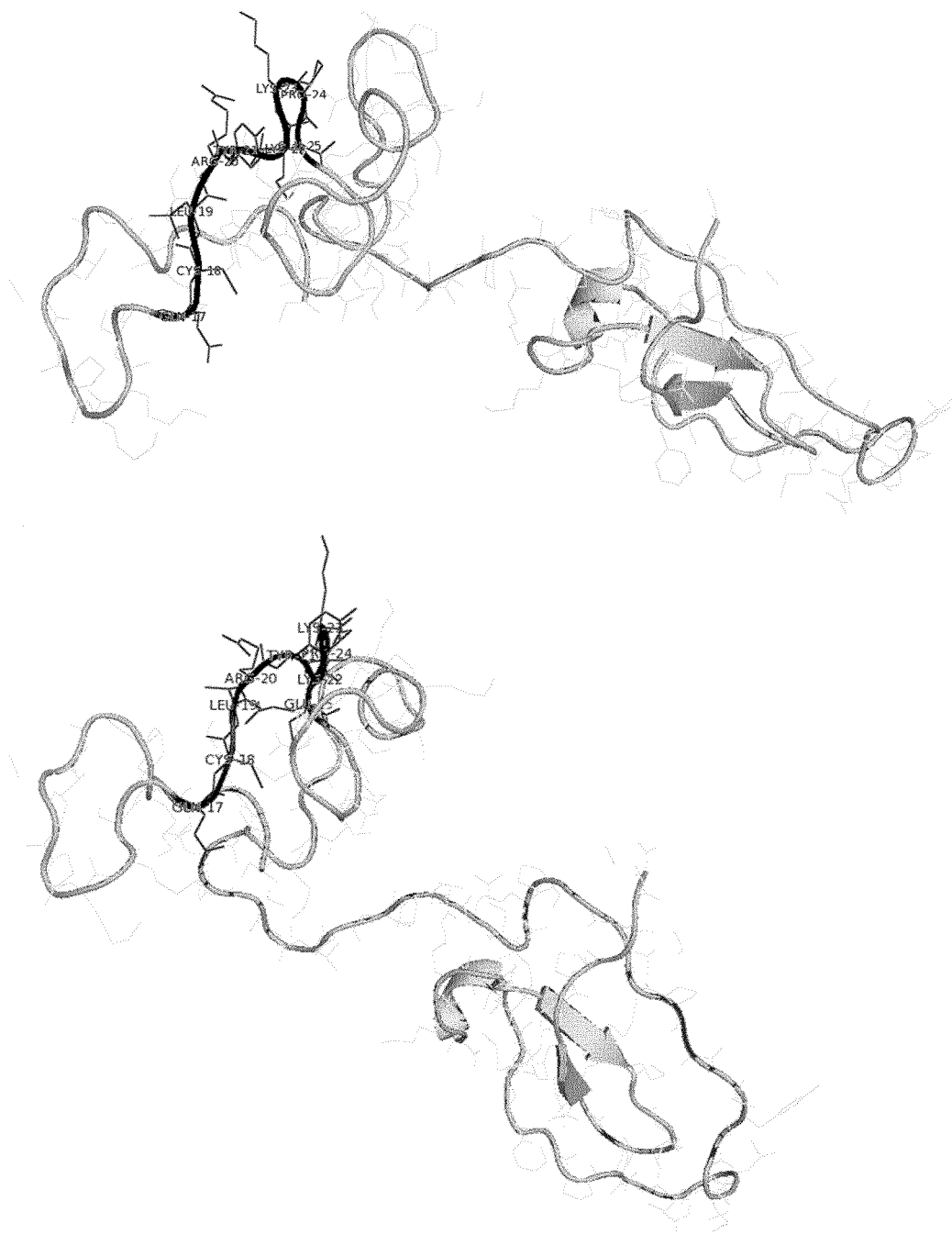

FIG. 6. In silico model of the mature SLPI peptide viewed in two separate orientations of SEQ ID NO: 2, confirming that the N-terminal hapten of SEQ ID NO: 5 is inaccessible (hapten highlighted in black).

Figure 7:
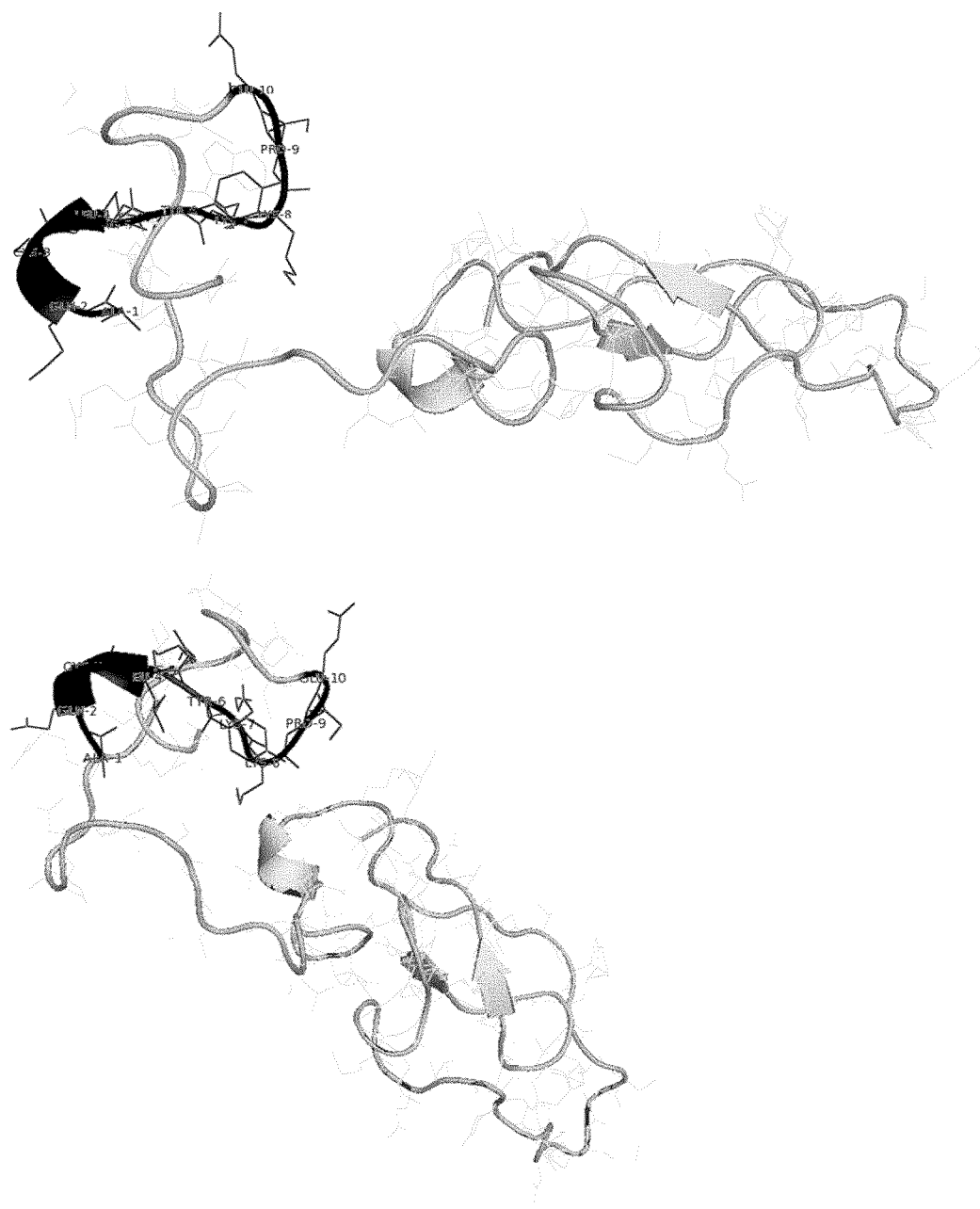

FIG. 7. In silico model of the C-SLPI viewed in two separate orientations of SEQ ID NO: 4, confirming that the N-terminal hapten of SEQ ID NO: 5 is accessible (hapten highlighted in black).

FIG. 8. C4.8 CDR sequencing. Graphical representation of the $V_H$ region of C4.8 (SEQ ID NO:7) showing the CDRs located between residues 27-38, 56-65 and 105-117 (highlighted in light grey) (A) and the $V_L$ region of C4.8 (SEQ ID NO:9) showing the CDRs located between residues 27-38, 56-65 and 105-117 (highlighted in light grey) (B).

Figure 9:
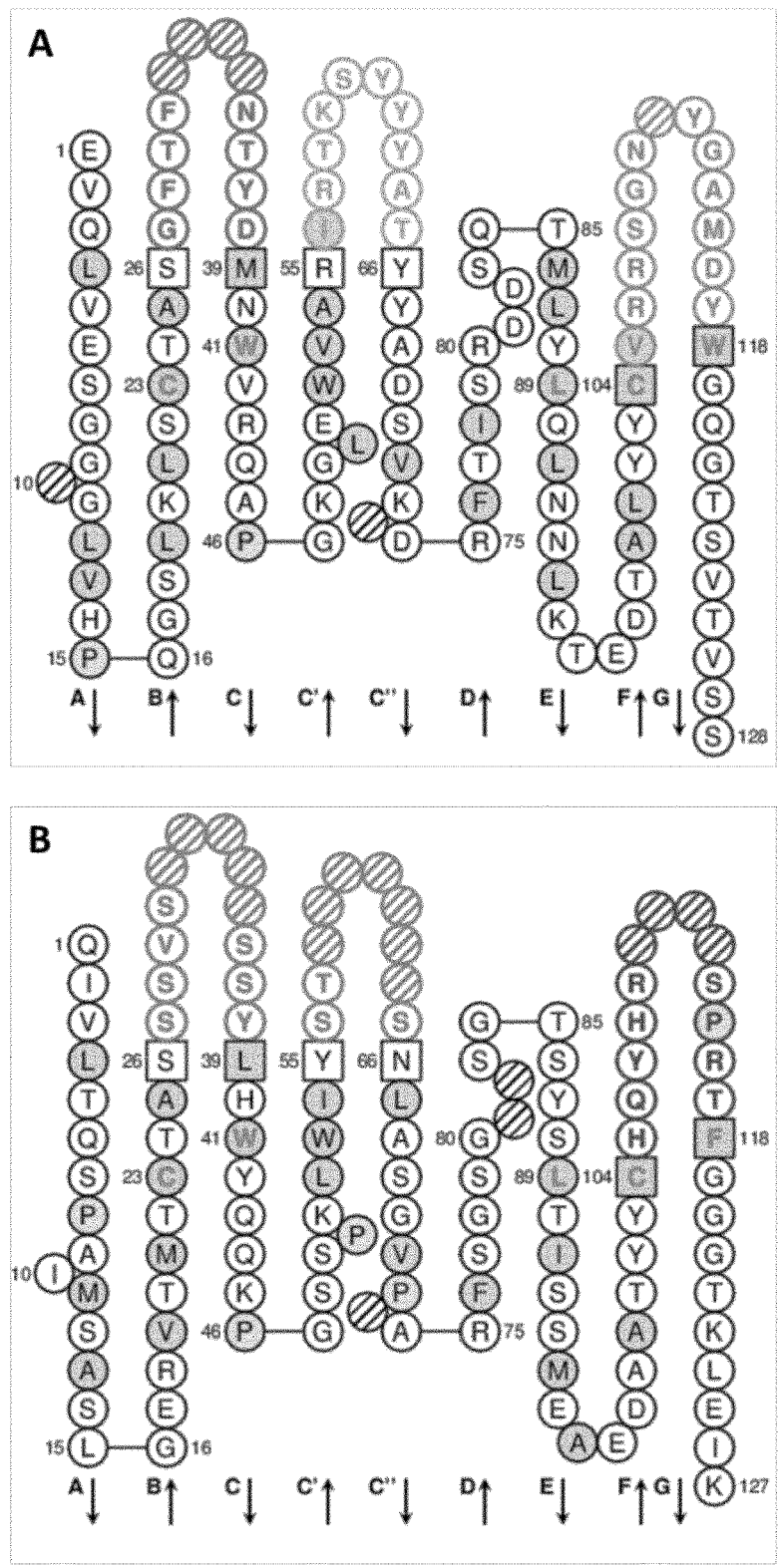

FIG. 9. C5.5 CDR sequencing. Graphical representation of the $V_H$ region of C5.5 (SEQ ID NO:8) showing the CDRs located between residues 27-38, 56-65 and 105-117 (highlighted in light grey) (A) and the $V_L$ region of C4.8 (SEQ ID NO:9) showing the CDRs located between residues 27-38, 56-65 and 105-117 (highlighted in light grey) (B).

FIG. 10. Alignment of C4.8 $V_L$ and $V_H$ domains with C5.5 $V_L$ and $V_H$ domains. There are sequence differences between the $V_H$ domains of C4.8 (SEQ ID NO: 7) and C5.5 (SEQ ID NO: 8). The $V_L$ domains of C4.8 and C5.5 (SEQ ID NO: 9) are identical.

FIG. 11. In silico modelling of the tertiary structure of the C-terminus of both SLPI and C-SLPI generated via Phyre2 software. The amino acid sequence used has an immunogen to generate monoclonal antibodies for the detection of C-SLPI, and therefore the antibody epitope, is highlighted in the figure in black. The sequence was shown to be exposed in C-SLPI (right) and un-exposed in full length SLPI (left).

Figure 12:
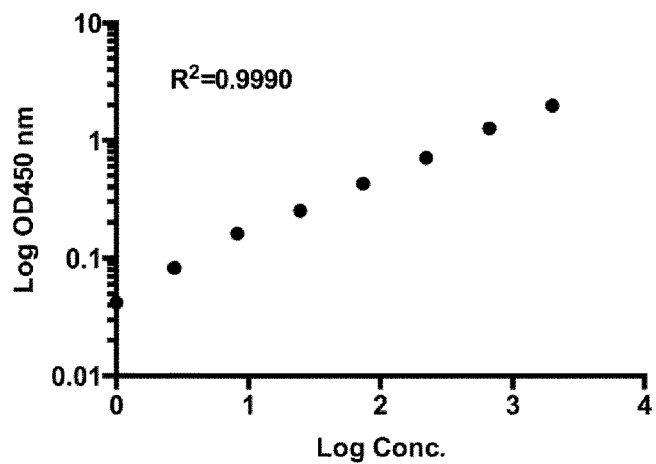

FIG. 12. Calibration curve generated from rC-SLPI ranging in concentration from 2000 ngml$^{-1}$ to 2.7 ngml$^{-1}$. $R^2$ value calculated via a four-parameter fit of the data.

Figure 13:
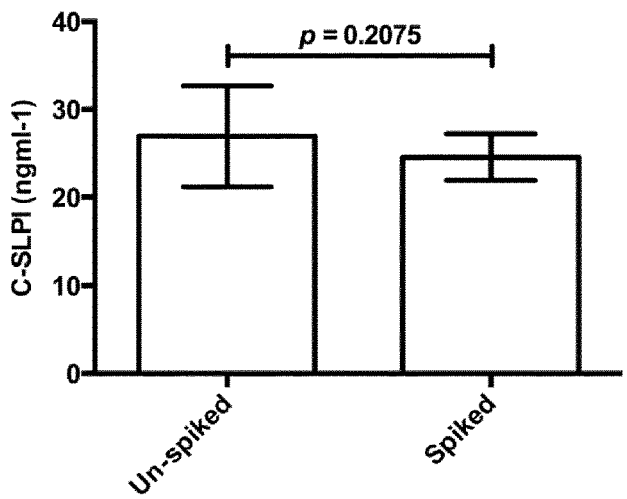

FIG. 13. Full length SLPI was spiked into a 24.69 ngml$^{-1}$ sample of rC-SLPI at a final concentration of 20,000 ngml$^{-1}$. To account for volume change, an equal volume of assay diluent was spiked into a separate 24.69 ngml$^{-1}$ sample of rC-SLPI. Both spiked and un-spiked samples were analysed using the C-SLPI ELISA. No significant difference in calculated concentration was observed between the spiked and un-spiked samples, (Un-paired two tailed T-test).

Figure 14:
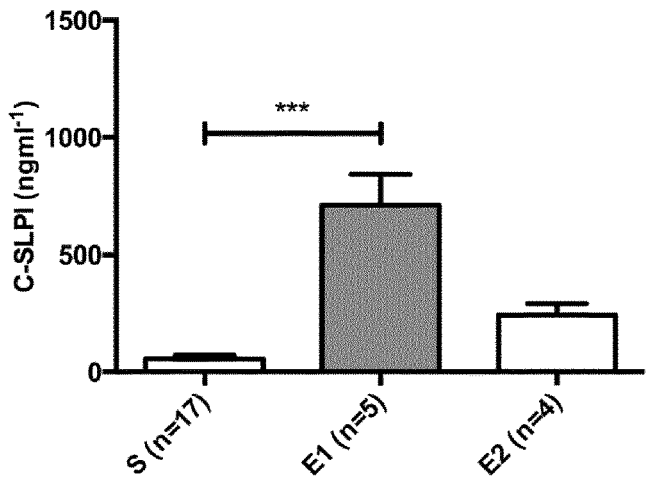

FIG. 14. C-SLPI was significantly increased in sputum samples from CF patients undergoing bacterial driven exacerbation (E1) compared with samples from CF patients in a stable condition (S). There was also an observed trend towards decreased C-SLPI in samples from patients being treated for exacerbation (E2) compared with samples from exacerbating patients (E1). (Kruskal-Wallis test with post-hoc Dunn's multiple comparison tests, ***p=≤0.001).

DETAILED DESCRIPTION OF THE INVENTION

Unless otherwise stated, technical terms are used according to the conventional usage as known to those skilled in the art.

A first aspect of the invention relates to a peptide hapten comprising the structure: Gln-Cys-Leu-Arg (SEQ ID NO: 10). Optionally, the hapten comprises, or consists of, the structure:

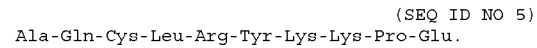

(SEQ ID NO 5)
    Ala-Gln-Cys-Leu-Arg-Tyr-Lys-Lys-Pro-Glu.

The term "hapten" as used herein describes a pre-immunogenic molecule that stimulates antibody production only when linked to a larger carrier molecule. For the purpose of this patent application, "linked" is synonymous with bound, attached, conjugated, crosslinked, coupled or chemically synthesised to.

The terms "peptide" and "polypeptide", can be used interchangeably and designate a chain of amino acid based polyamides. The chain can vary in length anywhere from 2 amino acids to 100 or more amino acids. Preferably the peptide is 5-12 amino acids in length and spans the region containing those N-terminal amino acids on cleaved C-SLPI (SEQ ID NOs: 3 and 4). Most preferably, the polypeptide is 5-10 or 11 amino acids in length. It will be appreciated that the haptens of the invention may be linked to a large carrier molecule, optionally via a crosslinking agent or via synthesis.

A second aspect of the current invention relates to an immunogen useful in the preparation of antibodies of the present invention which consists of a carrier molecule linked to either of the haptens described above.

The term "immunogen" as used herein, describes an entity that induces an immune response such as production of a T-cell response and antibodies in a host animal.

The term "carrier molecule" refers to a molecule to which a hapten or antigen can be linked to impart immunogenic properties to the hapten or antigen. The term "carrier molecule" may be used interchangeably with the terms "carrier", "immunogenicity conferring carrier molecule" and "antigenicity conferring carrier material".

Appropriate carrier materials commonly contain poly (amino acid) segments and include polypeptides, proteins and protein fragments. Illustrative examples of useful carrier materials are bovine serum albumin (BSA), egg ovalbumin (OVA), bovine gamma globulin (BGG), bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. Suitable carrier molecules include proteins such as bovine serum albumin, bovine thyroglobulin (BTG), ovalbumin, hemocyanin and thyroglobulin molecules as well as a branched lysine core, liposomes, synthetic or natural polymers and synthetically designed organic molecules. In this instance, a synthetic product MAPs (Multiple Antigenic Peptides), a multi-lysine product (branched lysine core), was the preferred carrier molecule (Posnett et al 1988).

The linking, or crosslinking, of haptens to carrier molecules to form an immunogen is well known in the art; the term "crosslinker" as used herein is any bifunctional molecule able to covalently join the hapten of the first aspect of the invention to an immunogenicity conferring carrier molecule. Posnett et al (1988), describe a carrier molecule referred to as MAPs to which multiple copies of the hapten according to the first aspect of the invention are linked via chemical synthesis, by the C-terminal amino acid of the hapten, to the lysine core (Posnett et al. 1988). A suitable crosslinker to link with alternative carrier molecules is maleimide, or a maleimide derivative, for example when BTG-maleimide is used to conjugate with the hapten via the cysteine residue. In this case, the hapten is coupled to a BTG maleimide carrier through the addition of a non-native cysteine. Although maleimides are the preferred cross-linking group, coupling with the sulfhydryl group of cysteine, other cross-linking groups which could couple this group on the cysteine include haloacetyls and pyridyldisulfides. Either Lys residue, or the Glu residue (C-terminal) may alternatively be used to conjugate to a carrier molecule, optionally via a crosslinking group, to form an immunogen. For example, a primary amine group on the side chain of lysine (Lys) could be coupled using a cross-linker selected from N-hydroxysuccinimide esters, imidoesters, PFP esters or hydroxymethyl phosphine. As another example, glutamic acid (Glu) could be coupled using a carbodiimide crosslinker, 1-Ethyl-3-(3-dimethylaminopropyl)carbodiimide (EDC) or N,N'-Dicyclohexylcarbodiimide (DCC). In one embodiment, the cross-linking group may comprise or consist of a carboxyl, dithiopyridyl, maleimidyl, amino, hydroxyl, thiol and aldehyde moiety. The cross-linking group is well known to the skilled person in immunogen synthesis.

A third aspect of the present invention describes an antibody or antigen binding fragment that specifically binds to C-SLPI selected from the group consisting of SEQ ID NOs: 3 and 4. In one embodiment, the antibodies of the present invention can bind SLPI which had been cleaved with NE which would result in a mixture of both C-SLPI species. Such a binding specificity, to one or both of the C-SLPI species, reflects the cleavage of SLPI in vivo. The antibody of the third aspect of the invention is raisable, or raised, from an immunogen of the second aspect of the current invention. The term "raisable" means that the antibody can be raised from an immunogen of the second aspect of the current invention but is not necessarily so raised. In this context, "raisable" includes, but is not limited to, "raised".

Optionally, the antibody is capable of binding, optionally specifically binding, to an epitope of C-SLPI, the epitope comprising SEQ ID NO: 6.

In one embodiment, the antibody, or antigen binding fragment, of the present invention has:
(A) a light chain CDR1 has the sequence SSVSSSY (SEQ ID NO: 11);
(B) a light chain CDR2 has the sequence STS; and
(C) a light chain CDR3 has the sequence HQYHRSPRT (SEQ ID NO: 13).

In another embodiment, the antibody, or antigen binding fragment thereof, of the present invention has:
(A) a heavy chain CDR1 has the sequence EYEFPSHD (SEQ ID NO: 14);
(B) a heavy chain CDR2 has the sequence INSDGGST (SEQ ID NO: 15); and
(C) a heavy chain CDR3 has the sequence ARQYYRG (SEQ ID NO: 16).

In yet another embodiment, the antibody, or antigen binding fragment thereof, has:

(A) a heavy chain CDR1 has the sequence GFTFNTYD (SEQ ID NO: 17);
(B) a light chain CDR2 has the sequence IRTKSYYYAT (SEQ ID NO: 18); and
(C) a light chain CDR3 has the sequence VRRSGNYG-AMDY (SEQ ID NO: 19).

In yet another embodiment, the antibody, or antigen binding fragment thereof, of the present invention has a $V_H$ region of SEQ ID NO 7 or 8. In yet another embodiment, the antibody, or antigen binding fragment thereof, of the present invention has a $V_L$ region of SEQ ID NO 9.

In yet another embodiment, the present invention is an antibody, or antigen binding fragment thereof, that crossblocks binding of the antibodies described above.

Optionally, the antibody is immobilised to a solid support. Further optionally, the solid support is selected from plastic or magnetic beads, polystyrene microtitre plates (ELISA plates), planar nitrocellulose, a ceramic biochip, and a biochip such as a plastic or glass.

The term "specifically" implies that the antibodies of the invention almost exclusively bind to a molecular structure contained within, and common to, the aforementioned C-SLPI; this can be verified by calculating suitable metrics such as the sensitivity and cross-reactivity. The analyte with the greatest cross-reactivity is given a value of 100%, with all other analytes accorded a value relative to this. As is recognised by the skilled person, the antibody will also bind to other molecules to a certain extent; the important aspect for the validity of an immunoassay using the antibody is that the binding of the antibody to non-target molecules is at a relatively low level. The cross-reactivity of this extraneous binding by non-target molecules in the immunoassay incorporating the antibody is often less than about 10% and is frequently immeasurable.

The skilled person would recognise that the structures of SLPI and C-SLPI differ in terms of the N-terminal fragment that is cleaved off during the formation of C-SLPI. The skilled person would also recognise that a C-SLPI antibody of the invention is recognising an epitope that is not shared by SLPI and C-SLPI, in other words those amino acids of SEQ ID NO: 6 that are shared by the two species of C-SLPI (namely SEQ ID NO:6) and, as will be shown hereinafter, are accessible in C-SLPI.

The term "antibody" refers to an immunoglobulin or immunoglobulin-like molecule. In a preferred embodiment of the current invention, the antibody is a monoclonal antibody but the skilled person will understand that any type of immunoglobulin molecule or fragment thereof can be used, for example polyclonal, monoclonal, humanised, chimeric, Fab fragments, short-chain or single chain variable fragments, all of which fall within the scope of the current invention. Monoclonal antibodies may be produced by methods known to those skilled in the art, such as but not limited to the method described herein. Any suitable host animal may be used for example, but not limited to sheep, rabbit, mouse, guinea pig or horse. The preferred animal used for immunisation in the current invention is a mouse. Freund's complete adjuvant was used as an immunopotentiator in the primary immunisations while Freund's incomplete adjuvant was used in all subsequent boosts. Those skilled in the art will know that any suitable immunopotentiator can be used in the initial immunisation and any further boosts.

Antibodies are composed of four polypeptide chains (two identical heavy chains and two identical light chains). Each chain has an antigen binding fragment comprising two domains: a variable domain (VH, VL) and a constant domain (CH, CL). The variable domains are attached to the constant domains. As the name implies, the variable domains vary in their amino acid sequence from one antibody molecule to another, providing the vast diversity the immune system needs to fight foreign invaders. The antigen binding site is formed where a heavy chain variable domain (VH) and a light chain variable domain (VL) come close together. These parts show the biggest difference among different antibodies.

The antibody is preferably a monoclonal antibody. The antibodies of the invention can be adsorbed on or covalently attached to a substrate. The substrate can be any substance or shape to which an antibody or antibody derivative can bind, either through chemical bonds (before which the substrate has to be chemically activated) or passive adsorption through mutual attraction of the substrate and antibody. Preferably, the antibodies are chemically bonded to the chemically activated substrate. The substrate can be for example plastic or magnetic beads, polystyrene microtitre plates (ELISA plates), planar nitrocellulose, a ceramic biochip or a biochip such as a plastic, glass or ceramic biochip surface-coated with a material that facilitates the immobilisation of the antibodies to the substrate. The antibodies or the substrate comprising the antibodies can be provided as discrete off-the-shelf reagents or be incorporated in a kit which optionally has other components such as a conjugate and/or calibrators.

A further aspect of the invention is a kit comprising the antibody (or antibodies) of the invention. Optionally, the kit further comprises a conjugate, a calibrator, and instructions for use Another aspect of the current invention relates to a method of detecting and/or determining C-SLPI selected from the group consisting of SEQ ID NOs: 3 and 4 in a sample.

The term "detecting" refers to qualitatively analysing for the presence or absence of a substance, while "determining" refers to quantitatively analysing for the amount of a substance present. The sample can be any biological fluid or sample in which C-SLPI, is found or expected. The method is preferably an ELISA but any suitable immunoassay method may be used, for example, a radioimmunoassay, magnetic immunoassay or a lateral flow test. The antibody can be attached to a solid support, for example, a biochip. The antibody specific for C-SLPI may be used in the assay on its own or with a secondary generic SLPI detection antibody i.e. an antibody which binds both SLPI and C-SLPI.

An example of the ELISA method comprises antibody specific for C-SLPI as the capture antibody and a labelled secondary generic SLPI antibody as the detector. The label of the labelled conjugate is a detectable label such as an enzyme, a luminescent substance, a radioactive substance or a mixture thereof. The preferred label is horseradish peroxidase. In one embodiment, the presence of the label can be determined by a colour change in response to reaction of the labelling agent with a substrate. In one embodiment, the colour change is determined by reading the absorbance at 450 nm. The detector antibody conjugated to the detectable label described above is an example of a detecting agent for use in the methods of the invention, but any suitable detecting agent can be used. The antibodies of the invention recognise a specific epitope of C-SLPI; another example of a suitable detecting agent is a monoclonal antibody attached to a detectable label, the monoclonal antibody being specific to a different epitope of C-SLPI. The antibody of the invention that is specific for C-SLPI can be combined with one or more other antibodies that detect different analytes as part of a multi-analyte immunoassay.

The format of an immunoassay for detecting or quantifying C-SLPI can be singleplex or multiplex; a singleplex immunoassay implies that only C-SLPI can be detected, while a multiplex immunoassay implies that one or more analytes other than C-SLPI can be detected. Generally, in a multiplex format, each analyte is detected by different antibodies, each antibody specific to an individual analyte or to structurally similar analytes (as in C-SLPI).

One advantage of the methods of the present invention is the speed at which C-SLPI can be detected or determined. In one embodiment, C-SLPI can be detected or determined using the methods of the present invention in between about 2 hours and about 10 minutes, between about 1 hour and about half an hour. In one embodiment, C-SLPI can be detected or determined using the methods of the present invention in about 30 minutes.

The invention also describes the use of the antibody of the invention in determining an individual's C-SLPI level as an indicator of susceptibility to, diagnosis of, and/or progression of a disease state. The disease state can be any in which C-SLPI has been implicated as a risk indicator or factor including bacterial infections, optionally respiratory bacterial infections. The disease state can also be sepsis.

Another aspect of the current invention relates to the use of the antibody of the invention in determining levels of C-SLPI in a sample from a person suspected of having a disease condition, in which the C-SLPI concentration differs in the disease state when compared to a control or normal range of expression. The sample may be any biological sample including, but not limited to, whole blood, plasma, serum, sputum, broncho-alveolar lavage (BAL) or saliva.

Thus, the invention also relates to methods utilising the antibody for (a) evaluating an individual's susceptibility to disease; (b) disease diagnosis and prognosis; and/or (c) monitoring of a disease.

The invention also relates to methods and kits that facilitate a more rapid testing of bacterial infection status, for example to detect bacterial infection or exacerbation in patients with chronic infective lung disease, including, but not limited to, CF.

The invention also relates to methods and kits that facilitate monitoring the progression of bacterial infection, for example to monitor bacterial infection or exacerbation in patients with chronic infective lung disease, including, but not limited to, CF.

By "progression" is meant herein, monitoring the response/non-response of a patient to a therapeutic treatment from a first timepoint to a later timepoint by
  providing a first biological sample obtained at the first timepoint,
  measuring the concentration of C-SLPI in said biological sample,
  providing a second biological sample obtained at the later timepoint,
  measuring the concentration of C-SLPI in said second biological sample, and
  determining the difference in concentration of C-SLPI between the first and second biological samples, wherein a higher concentration at the second timepoint is indicative of bacterial driven exacerbation and a lower concentration at the second timepoint is indicative of responding to therapy for bacterial driven exacerbation.

These novel antibodies could also be employed on various diagnostic platforms to detect bacterial infection or exacerbation in patients with chronic infective lung disease such as, but not limited to, CF.

Enzyme Immunoassays, ELISAs

The enzyme-linked immunosorbent assay (ELISA) is a test that uses antibodies and colour change to identify a substance.

Antigens from the sample are attached to a surface. Then, a further specific antibody is applied over the surface so it can bind to the antigen. This antibody is linked to an enzyme, and, in the final step, a substance containing the enzyme's substrate is added. The subsequent reaction produces a detectable signal, most commonly a colour change in the substrate.

Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed to remove any proteins or antibodies that are not specifically bound. After the final wash step, the plate is developed by adding an enzymatic substrate to produce a visible signal, which indicates the quantity of antigen in the sample.

Lateral Flow Devices

In recent years, the in vitro diagnostics industry has made enormous efforts to develop immunochromatographic tests. Such tests have found applications in both clinical and non-clinical fields. A clinical utility of this test format is particularly suited to point of care utilities.

Rapid immunochromatographic test devices, e.g. in the form of a test strip, are made up of a number of components. Such a test strip commonly includes a sample pad, a conjugate pad, a membrane, e.g. a nitrocellulose membrane, and an absorbent pad. The membrane is usually attached by means of an adhesive to a supporting backing, e.g. made of plastic. In practice, the user dispenses a patient sample (such as urine or whole blood) onto the sample pad. The sample then flows through the sample pad into the conjugate pad, where it mixes with, and releases, the detector reagent. This mixture then flows across the membrane, where it binds with the test and control reagents located in the capture test zone (sample zone) and negative control zone, respectively. When the mixture binds to the reagent that forms the test line, a positive result is indicated. The colour intensity of the test line is proportional to the concentration of analyte in the sample. Excess sample that flows beyond the test and control zones is taken up in the absorbent pad.

Rapid immunochromatographic test devices for diagnostic purposes are easy to operate and thus do not only contribute to the comfort of professional users, e.g. medical stuff, but also allow the operation by non-professionals users, e.g. most patients.

Biochips

Biochips are components used for example in chemical analysis (including Proteomic and Molecular analysis) either to host a test reaction and/or to supply samples under test or reagents. Generally, a Biochip comprises a solid substrate, on which is arranged one or more test sites at which a reaction can take place in use. For instance, the test site may carry one or more reagents (e.g. ligands such as antibodies or antigens) adsorbed to the substrate, which are activated by the addition of a sample substance (e.g. analytes present in the sample bind to specific ligands). Such chips are sometimes referred to as a "lab on a chip" and can also incorporate tools for controlling steps of a reaction. As an example, one Biochip supplied by Randox Laboratories Limited (55 Diamond Road, Crumlin, County Antrim, United Kingdom, BT29 4QY) is used as a medium for performing multiplex analysis of biological samples using a chemiluminescence method. In this example, the Biochip takes the form of a small ceramic chip with a specialised surface preparation which is sensitive to environmental degradation. Therefore the Biochip is generally delivered in an environmentally sealed format, usually evacuated, sealed foil bags.

For instance, the Evidence™ analyser by Randox Laboratories Ltd uses biochips which are fitted into a plastic holder defining three recesses arranged in a line. Each recess is approximately square and sized to just accommodate a biochip, which is also square, with a small clearance to allow the chip to be placed. The "strip" of three mounted biochips is placed within a sealed foil bag for storage, which is then opened when the biochips are required for use. The plastic holder may be placed on a carrier alongside two further strips of three biochips to form a 3–3 array of biochips. The carrier has a keying feature for engagement with a robotic arm such that the array can be transported within the analyser via robotic handling. This configuration is useful for batch analysis.

A "Biochip" is a general term for a reaction platform for hosting chemical, biochemical, proteomic or molecular tests, as may be required for medical diagnosis, drug detection, etc. Typically, a Biochip comprises an inert substrate, such as silicon or glass (often of the order of about 1 $cm^2$ or less in surface area), on which one or a plurality of reaction sites is provided. The sites generally carry one or more ligands, for example, one or more antibodies, selected for the test (or "assay") to be performed, adsorbed to the surface of the chip for activation upon combination with a sample applied to the chip (e.g. a blood sample) and/or a reagent. The reactions can be detected using a number of alternative techniques, including detection of chemiluminescence generated by the reaction. Some biochips carry a very large number (hundreds or thousands) of such tests sites, typically arranged in a grid or array, making it possible to carry out numerous assays simultaneously, and using the same single specimen.

GENERAL METHODS, EXAMPLES AND RESULTS

Materials and Methods

Materials

Recombinant human SLPI was purchased from R&D Systems of 614 McKinley Place Nebr., Minneapolis, Minn. 55413, USA (product number: 1274-PI-100). Biotinylated anti-human SLPI PAb was purchased from R&D Systems (Catalogue: BAF1274; immunogen: E. coli-derived recombinant human SLPI; source: polyclonal goat IgG; purification: antigen affinity-purified). N-(methoxysuccinyl)-Ala-Ala-Pro-Val-chloromethyl ketone (MeOSuc-AAPV-CMK; SEQ ID NO: 12) was purchased from Sigma-Aldrich (product number: M 0398). MeOSuc-AAPV-CMK is an inhibitor of human leukocyte elastase (HLE). N-(methoxysuccinyl)-Ala-Ala-Pro-Val-amino-4-methylcoumarin (MeOSuc-AAPV-AMC; SEQ ID NO: 20) was purchased from Enzo Life Sciences (product number: P-224). MeOSuc-AAPV-AMC is a highly sensitive substrate for HLE. Human NE was purchased from Elastin Products (product number: SE563). HRP-conjugated streptavidin was obtained from BioLegend of 4B Highgate Business Centre, London, NW5 1LB, UK (product number: 405210).

Generation of Hybridoma Cell Lines

C-SLPI hybridoma cell lines were generated by initially inoculating mice with an immunogen comprising AQCL-RYKKPE of SEQ ID NO: 5, linked to MAPs, as described in Posnett et al 1988, in which the carrier molecule comprises MAPs and multiple copies of the hapten of SEQ ID NO: 5 are linked, by the C-terminal amino acid of the hapten, to the branched MAP core. B-cells from the spleens of inoculated mice were fused with a myeloma cell line to produce hybridomas which were sub-cloned to give rise to a number of clone lines producing antibody to C-SLPI.

Culturing of C-SLPI Hybridoma Cell Lines

Hybridoma cell lines were routinely cultured in high glucose DMEM media (PAA) supplemented with 10% Fetal Calf Serum (FCS) (Gibco), 1×HT Media Supplement Hybri-Max (Sigma Aldrich) and Penicillin-Streptomycin L-glutamine (Sigma Aldrich). Cells were broken out of liquid nitrogen storage into 1 ml cultures on a 24 well culture plate using a log dilution down each column of the plate. Viable cultures were subsequently expanded into 5 ml, 30 ml, 80 ml and 200 ml cultures. Supernatant from 200 ml cultures was removed via centrifugation of the culture at 1400 rpm for 5 min and stored at −20° C.

Generation of C-SLPI

C-SLPI was generated by incubating 50 ng of recombinant human SLPI (R&D) with human sputum derived NE (Elastin Products) at molar ratios of 1:1, 1:2, 1:4, 1:8 and 1:10 (SLPI:NE) for 16 h in 0.1 M HEPES/0.5 M NaCl (pH7.5) in a 20 µl final volume at 37° C. Elastase activity was neutralized with 1 µl of MeOSuc-AAPV-CMK (100 mM) for 30 min at room temperature (Weldon et al. 2009).

Western Blot Analysis of C-SLPI

Individual C-SLPI incubation samples (20 µl) were profiled on a denaturing SDS-PAGE using 17% polyacrylamide and blotted onto nitrocellulose membrane (Sigma-Aldrich). The membrane was blocked for 1 h at room temperature with 5% BSA in PBS containing 0.1% (v/v) Tween 20. C-SLPI was detected using a biotinylated anti-SLPI Ab provided by R&D Systems (1/500 v/v in 5% BSA in PBS containing 0.1% (v/v) Tween 20, overnight at 4° C. with shaking) followed by incubation with HRP-conjugated streptavidin provided by BioLegend (1/2000 v/v in PBS, 20 min at room temperature). Peroxidase activity was detected using the chemiluminescent Western Lightning Plus ECL substrate (PerkinElmer) and analyzed using the Syngene GeneSnap and Gene Tools software on the ChemiDoc system (Weldon et al. 2009).

ELISA Detection of C-SLPI

A Maxisorp plate (Nunc) was coated for 16 h at 4° C. with 100 µl/well hybridoma supernatant diluted 1:50 in Voller's reagent. Cell free hybridoma supernatants were acquired directly from individual cultures by centrifugation at 1,400 rpm for 5 min. The plate was blocked with 200 µl 1% BSA in PBST 0.05% (v/v) Tween 20 for 1 h at room temperature. Either a half concentration dilution series of 200 ng/ml to 3.125 ng/ml of both C-SLPI and SLPI (100 µl/well) in 1% BSA in PBST 0.05% (v/v) Tween 20 or CF sputum samples diluted 1:50 v/v in 1% BSA in PBST 0.05% (v/v) Tween 20 were added to the plate and incubated for 2 h at room temperature. Control wells received NE alone. The plate was washed three times with PBS/0.05% (v/v) Tween before adding biotinylated anti-SLPI IgG BAF1274 (1/500 v/v in 1% BSA in PBST 0.05% (v/v) Tween 20; R&D systems) and incubating for 2 h. After washing three times, streptavidin peroxidase (1/2000 in PBS; BioLegend) was added to the plate for 40 min. After washing three times, ABTS single solution substrate (Zymed Laboratories) was added and the plate was incubated at room temperature for 15 min. The absorbance at 405 nm of wells was measured on a microtiter plate reader (Genios using Magellan software) and results were analyzed using GraphPad Prism version 6 (GraphPad Software).

C-SLPI Antibody Purification

C-SLPI antibody was purified from cell free hybridomas culture supernatant obtained via centrifugation at 1,400 rpm for 5 min. The culture supernatant was then concentrated to a feedstock of approximately ⅙ initial volume via haemodialysis. The feed stock was then adjusted to a pH of 7.2 and applied to a Protein G Sepharose 4 Fast Flow column (GE Healthcare) which had been pre washed with PBS at pH 7.2. After flow through of feed stock was completed unbound or weekly bound material was removed from the column by applying 10 column volumes of washing buffer (1 M Phosphate buffer at pH 7.5). Elution of antibody from the column was achieved via the application of elution buffer (100 mM Glycine-HCl, pH 2.7) to the column with antibody elution being monitored by UV spectrophotometry using a UV MII spectrophotometer coupled to a REC112 chart recorder (both Amersham Biosciences). The eluted antibody was then concentrated via dialysis in PBS.

NE (Neutrophil Elastase) Activity Assay

To determine the NE activity in samples (for example, CF and asthma sputum samples), 10 µl of sample was diluted with 40 µl 0.1 M Hepes, 0.5 M NaCl, pH 7.5 and incubated for 30 min at 37° C. for 30 min. Activity of NE was determined spectrophotometrically by adding 50 µl of 3 mM MeOSuc-AAPV-AMC and measuring the absorbance at 405 nm over the time at 37° C.

Complementary Determining Region (CDR) Sequencing

CDR sequencing was carried out externally by Fusion Antibodies Ltd. (Belfast, UK). mRNA was extracted from a cell pellet derived via centrifugation for a 30 ml hybridomas culture using an in house RNA extraction protocol. This mRNA was utilised as a template to produce cDNA via reverse transcription using an oligo (dT) primer. The cDNA was in turn used as a template for the amplification of the $V_H$ (Variable domain, heavy chain) and $V_L$ (Variable domain, light chain) genes using Fusion Antibodies monoclonal sequencing primers. The PCR reactions were analysed by agarose gel electrophoresis and the positive PCR products identified. These were then sequenced using the individual primers as used in the respective PCR reactions. The DNA sequences obtained for both the $V_H$ and $V_L$ genes were separately aligned to provide a consensus sequence for each gene which was translated in silico to obtain a peptide sequence for both the $V_H$ and $V_L$ regions. The CDRs were determined by the IMGT numbering system, (Lefranc et al. 1999). VH and VL sequeces provided by Fusion Antibodies were assayed for sequence uniqueness via Basic Local Alignment Search Tool (BLAST) analysis against both the Swiss-prot database and patented peptide sequences deposited in the Genbank database.

Results

Generation of Hybridoma Cell Lines

A number of hybridoma clone lines were produced via inoculation of mice with an immunogen of SEQ ID NO: 5 linked to a MAP product (Posnett et al. 1988). Two clones—C5.5 and C4.8—were shown to have positive activity against C-SLPI and little cross-activity against SLPI. Clones C5.5 and C4.8 were successfully cultured in increasing volumes to a maximum of 200 ml, supernatant collected and stored at −20° C.

Generation of C-SLPI

C-SLPI was generated via incubation of recombinant mature SLPI of SEQ ID NO: 2, with human sputum derived NE. A number of differing molar ratios of SLPI to NE were tested in order to establish an optimal incubation reaction using 50 ng of SLPI in all reactions. Successful cleavage of SLPI was eluded via Western blot analysis. Molar ratios of SLPI to NE of 1:4 to 1:10 was found to be sufficient to generate C-SLPI with the most optimal ratio being 1:10 (FIG. 1). C-SLPI used in subsequent experiments was produced using this molar ratio of SLPI to NE.

Testing of Culture Supernatant from C-SLPI Hybridomas

Supernatant from C5.5 and C4.8 showed activity against C-SLPI with absorbance decreasing in a dose dependent manner as C-SLPI concentration decreased, (FIGS. 2 and 3). The low cross-reactivity with mature SLPI of SEQ ID NO: 2 or NE was deemed to be 'background only' and did not increase across the range of SLPI concentrations tested (FIGS. 2 and 3).

Testing of C5.5 Supernatant with CF Sputum Samples

Supernatant from C5.5 culture was used to detect C-SLPI in sputum samples from 63 CF patients via ELISA. C5.5 supernatant was able to detect C-SLPI in a number of CF samples (FIG. 4). In addition to using C5.5 supernatant to detect C-SLPI in the CF sputum samples, NE activity within the samples was measured using a fluorescently tagged substrate. There was no statistically significant direct correlation but this did trend toward statistical significance (FIG. 5). We envisage that an increase in the numbers of samples being evaluated will lead to a significant p value.

In Silico Modelling

FIG. 6 shows an in silico model of the mature human SLPI peptide SEQ ID NO: 2 with the hapten of SEQ ID NO: 5. FIG. 7 shows an in silico model of the C-SLPI of SEQ ID NO: 4, suggesting that the hapten of SEQ ID NO: 5 is accessible. The in silico model of FIG. 7 supports the empirical finding that the antibodies of the present invention bind specifically to the exposed N-terminal region of C-SLPI.

CDR Sequencing

The amino acid sequences of the $V_H$ region for C4.8 and C5.5 are listed as SEQ ID NO 7 and SEQ ID NO 8 respectively. The amino acid sequences of the $V_L$ region for C4.8 and C5.5 are listed as SEQ ID NO 9. The identified CDRs for both C5.5 and C4.8 are highlighted in bold text. BLAST analysis of these sequences show the $V_H$ and $V_L$ regions to be unique for each hybridoma clone. This level of uniqueness extends to the CDR level with differences in the CDRs of both hybridomas clones being identified when compared to both the Uniprot database and previously patented sequences on the NCBI database. A graphical representation of the $V_H$ and $V_L$ regions of C4.8 and C5.5 can be seen in FIG. 8 and FIG. 9 respectively. When the sequences of the $V_H$ and $V_L$ regions of C4.8 and C5.5 were aligned against each other, it was found that the $V_H$ regions of the two antibodies differed however the $V_L$ regions were identical in sequence, FIG. 10.

Cystic Fibrosis (CF) is a debilitating hereditary disease in which the lungs produce thick sputum that is difficult to clear and is classically associated with chronic bacterial infection resulting in an increased, detrimental inflammatory response. One such effect of this chronic infection is disruption of the body's natural defence to proteases; the antiprotease screen. One antiprotease that is affected is human Secretory Leucocyte Protease Inhibitor (SLPI). SLPI is an 11.7 KDa cationic serine protease inhibitor that, following posttranslational modification, consists of 107 amino acid residues and possesses two Whey Acidic Protein domains. SLPI can be found in a variety of patient samples and is produced by a number of cell types including neutrophils, macrophages and epithelial cells. SLPI is expressed in response to various stimuli such as bacterial lipopolysaccharides, human neutrophil elastase (HNE) and a number of cytokines. SLPI has both antiprotease activity against HNE and cathepsin G, mediated via its C-terminal domain. SLPI also possesses anti-microbial activity against Gram negative and Gram positive organisms which is mediated by its N-terminal domain. Previous research has shown that, when CF patients are chronically infected with *Pseudomonas aeruginosa*, SLPI is reduced in the Bronchoalveolar Lavage fluid (BALF). Further investigation demonstrated that SLPI was being cleaved due to the excess levels of HNE resulting from the recruitment of activated neutrophils to the sites of infection. C-SLPI was shown to have reduced biological activity when compared with full length SLPI.

Relevance

The current methodology of testing for bacterial infection during an exacerbation in CF patients involves classical culture-driven microbiological techniques which can take up to 48 hours to generate a result. The availability of rapid, less laborious tests will facilitate a more efficient diagnosis leading to quicker treatment strategies to reduce the pathological burden of infection within CF patients. The generation of C-SLPI has been specifically shown to be related to bacterial infection with *P. aeruginosa*, a bacterium highly associated with chronic infection in CF and detrimental exacerbations. Based on this connection, it is reasonable to hypothesise that C-SLPI can act as a biomarker of exacerbation as a result of chronic bacterial infection in CF patients. The aim of this study was to generate monoclonal antibodies for the development of efficient immunoassays based on the detection of C-SLPI as a potential biomarker for bacterial infection.

Methodology

An amino acid sequence within C-SLPI was used as an immunogen to produce hybridoma clones expressing monoclonal antibodies to C-SLPI. Basic Local Alignment Search Tool (BLAST) analysis of the immunogen against the Pfam protein families database was performed as was in silico modelling of the predicted C-SLPI epitope (FIG. 11). Monoclonal antibodies purified from the supernatants of these hybridoma clones via affinity chromatography were assessed by ELISA for activity against both C-SLPI and full-length SLPI and antibodies recognising specifically C-SLPI were selected. Additionally, 26 CF patient sputum samples were assayed.

Results

Respectively, BLAST analysis and in silico modelling showed the immunogen to be specific for C-SLPI and that the epitope bound by the C-SLPI monoclonal antibodies is exposed on the C-SLPI peptide but not on full length SLPI. This appears to be due to the breakage of a di-sulphide bond during the HNE cleavage event. Using a C-SLPI monoclonal antibody purified from supernatants of the hybridoma clone lines paired with a conjugated detector antibody and using recombinant C-SLPI as calibrator material, we have demonstrated, via ELISA, the ability to detect C-SLPI ranging in concentration from 2.70 $ngmL^{-1}$ to 2000 ngmL$^{-1}$ (FIG. 12). Additionally the cross-reactivity of the C-SLPI monoclonal antibody with full-length SLPI was demonstrated to be <0.05% indicating high specificity for C-SLPI (FIG. 13). Initial analysis via ELISA of sputum samples from CF patients experiencing an exacerbation showed statistically significantly higher levels of C-SLPI antigen when compared to those patients who were not experiencing an exacerbation and a trend towards a fall in C-SLPI when samples from exacerbating patients were compared with samples from patients receiving antimicrobial therapy for exacerbation (FIG. 14).

CONCLUSIONS

The results indicate the successful development of antibodies applicable to the development of efficient immunoassays for the specific detection of C-SLPI. This is relevant in clinical settings to facilitate a more rapid testing of bacterial infection status. These novel antibodies could be employed on various diagnostic platforms to detect bacterial infection or exacerbation in patients with chronic infective lung disease.

REFERENCES

Doumas, S. & Kolokotronis, A., 2005. Anti-Inflammatory and Antimicrobial Roles of Secretory Leukocyte Protease Inhibitor MINIREVIEW Anti-Inflammatory and Antimicrobial Roles of Secretory Leukocyte Protease Inhibitor., 73 (3).
Gibson, G. J. et al., 2013. Respiratory health and disease in Europe: the new European Lung White Book. *European Respiratory Journal*, 42 (3), pp. 559-563. Available at: http://erj.ersjournals.com/content/42/3/559.abstract.
Hiemstra, P. S. et al., 1996. Antibacterial activity of antileukoprotease. *Infection and Immunity*, 64 (11), pp. 4520-4524. Available at: http://iai.asm.org/content/64/11/4520.abstract.
Kammouni, W. et al., 1997. *Pseudomonas aeruginosa* lipopolysaccharide induces CF-like alteration of protein secretion by human tracheal gland cells. *Biochemical and biophysical research communications,* 241 (2), pp. 305-11. Available at: http://www.sciencedirect.com/science/article/pii/S0006291X97977202 [Accessed Jul. 30, 2014].
Murray, T. S., Egan, M. & Kazmierczak, B. I., 2007. *Pseudomonas aeruginosa* chronic colonization in cystic fibrosis patients. *Current Opinion in Pediatrics,* 19 (1). Available at: http://journals.lww.com/co-pediatrics/Fulltext/2007/02000/Pseudomonas_aeruginosa_chronic_colonization_in.14.aspx.
Posnett, D. N., McGrath, H. & Tam, J. P., 1988. A novel method for producing anti-peptide antibodies. Production of site-specific antibodies to the T cell antigen receptor beta-chain. *Journal of Biological Chemistry,* 263 (4), pp. 1719-1725. Available at: http://www.jbc.org/content/263/4/1719.abstract.
Seemüller, U. et al., 1986. The acid-stable proteinase inhibitor of human mucous secretions (HUSI-I, antileukoprotease). *FEBS Letters,* 199 (1), pp. 43-48. Available at: http://www.sciencedirect.com/science/article/pii/0014579386812200 [Accessed Jul. 30, 2014].
Voynow, J. a, Fischer, B. M. & Zheng, S., 2008. Proteases and cystic fibrosis. *The international journal of biochemistry&cell biology,* 40 (6-7), pp. 1238-45. Available at: http://www.pubmedcentral.nih.gov/articlerenderfcgi?artid=2431113&tool=pmcentrez&rendertype=abstract [Accessed Jun. 13, 2014].
Weldon, S. et al., 2009. Decreased levels of secretory leucoprotease inhibitor in the *Pseudomonas*-infected cystic fibrosis lung are due to neutrophil elastase degradation. *Journal of immunology* (Baltimore, Md.: 1950), 183 (12), pp. 8148-56. Available at: http://www.pubmedcentral.nih.gov/articlerenderfcgi?artid=3404409&tool=pmcentrez&rendertype=abstract [Accessed Jun. 13, 2014].

We claim:

1. An immunogen comprising a polypeptide hapten of 5-12 amino acids in length comprising the structure Gln-Cys-Leu-Arg (SEQ ID NO: 10), wherein the N-terminus region of the polypeptide hapten comprises SEQ ID NO: 10; and wherein the polypeptide hapten is linked to an immunogenicity conferring carrier molecule by the C-terminal amino acid of the polypeptide hapten.

2. An antibody, or antigen binding fragment thereof, that is capable of specifically binding, to an epitope of C-terminal peptide fragment of Secretory leukocyte protease inhibitor (C-SLPI), the peptide fragment which is 10, 11 or 12 amino acids in length and comprises SEQ ID NO: 6 wherein the N-terminus region of the polypeptide fragment comprises SEQ ID NO: 6 and wherein the cross-reactivity of the antibody with full-length SLPI is <0.05%.

3. A method of determining an individual's C-SLPI level by:
   (a) contacting an antibody specific for C-terminal fragment of Secretory leukocyte protease inhibitor (C-SLPI) with a sample from the individual; and
   (b) detecting the amount of C-terminal fragment of Secretory leukocyte protease inhibitor (C-SLPI) in the sample;

wherein the cross-reactivity of the antibody with full-length Secretory leukocyte protease inhibitor (SLPI) is <0.05%.

* * * * *

SEQUENCE LISTING

```
<160> NUMBER OF SEQ ID NOS: 20

<210> SEQ ID NO 1
<211> LENGTH: 132
<212> TYPE: PRT
<213> ORGANISM: Homo sapiens

<400> SEQUENCE: 1

Met Lys Ser Ser Gly Leu Phe Pro Phe Leu Val Leu Leu Ala Leu Gly
1               5                   10                  15

Thr Leu Ala Pro Trp Ala Val Glu Gly Ser Gly Lys Ser Phe Lys Ala
            20                  25                  30

Gly Val Cys Pro Pro Lys Lys Ser Ala Gln Cys Leu Arg Tyr Lys Lys
        35                  40                  45

Pro Glu Cys Gln Ser Asp Trp Gln Cys Pro Gly Lys Lys Arg Cys Cys
    50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys
                85                  90                  95

Leu Met Leu Asn Pro Pro Asn Phe Cys Glu Met Asp Gly Gln Cys Lys
            100                 105                 110
```

Arg Asp Leu Lys Cys Cys Met Gly Met Cys Gly Lys Ser Cys Val Ser
            115                 120                 125

Pro Val Lys Ala
    130

<210> SEQ ID NO 2
<211> LENGTH: 107
<212> TYPE: PRT
<213> ORGANISM: Homo sapiens

<400> SEQUENCE: 2

Ser Gly Lys Ser Phe Lys Ala Gly Val Cys Pro Pro Lys Lys Ser Ala
1               5                   10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
        35                  40                  45

Asp Pro Val Asp Thr Pro Asn Pro Thr Arg Arg Lys Pro Gly Lys Cys
50                  55                  60

Pro Val Thr Tyr Gly Gln Cys Leu Met Leu Asn Pro Pro Asn Phe Cys
65                  70                  75                  80

Glu Met Asp Gly Gln Cys Lys Arg Asp Leu Lys Cys Cys Met Gly Met
                85                  90                  95

Cys Gly Lys Ser Cys Val Ser Pro Val Lys Ala
            100                 105

<210> SEQ ID NO 3
<211> LENGTH: 91
<212> TYPE: PRT
<213> ORGANISM: Homo sapiens

<400> SEQUENCE: 3

Gln Cys Leu Arg Tyr Lys Lys Pro Glu Cys Gln Ser Asp Trp Gln Cys
1               5                   10                  15

Pro Gly Lys Lys Arg Cys Cys Pro Asp Thr Cys Gly Ile Lys Cys Leu
            20                  25                  30

Asp Pro Val Asp Thr Pro Asn Pro Thr Arg Arg Lys Pro Gly Lys Cys
        35                  40                  45

Pro Val Thr Tyr Gly Gln Cys Leu Met Leu Asn Pro Pro Asn Phe Cys
50                  55                  60

Glu Met Asp Gly Gln Cys Lys Arg Asp Leu Lys Cys Cys Met Gly Met
65                  70                  75                  80

Cys Gly Lys Ser Cys Val Ser Pro Val Lys Ala
            85                  90

<210> SEQ ID NO 4
<211> LENGTH: 92
<212> TYPE: PRT
<213> ORGANISM: Homo sapiens

<400> SEQUENCE: 4

Ala Gln Cys Leu Arg Tyr Lys Lys Pro Glu Cys Gln Ser Asp Trp Gln
1               5                   10                  15

Cys Pro Gly Lys Lys Arg Cys Cys Pro Asp Thr Cys Gly Ile Lys Cys
            20                  25                  30

Leu Asp Pro Val Asp Thr Pro Asn Pro Thr Arg Arg Lys Pro Gly Lys
        35                  40                  45

Cys Pro Val Thr Tyr Gly Gln Cys Leu Met Leu Asn Pro Pro Asn Phe

```
                        50                  55                  60
Cys Glu Met Asp Gly Gln Cys Lys Arg Asp Leu Lys Cys Cys Met Gly
 65                  70                  75                  80

Met Cys Gly Lys Ser Cys Val Ser Pro Val Lys Ala
                 85                  90
```

```
<210> SEQ ID NO 5
<211> LENGTH: 10
<212> TYPE: PRT
<213> ORGANISM: Artificial Sequence
<220> FEATURE:
<223> OTHER INFORMATION: N-terminal hapten

<400> SEQUENCE: 5
```

```
Ala Gln Cys Leu Arg Tyr Lys Lys Pro Glu
 1               5                  10
```

```
<210> SEQ ID NO 6
<211> LENGTH: 9
<212> TYPE: PRT
<213> ORGANISM: Artificial Sequence
<220> FEATURE:
<223> OTHER INFORMATION: C-SLPI epitope

<400> SEQUENCE: 6
```

```
Gln Cys Leu Arg Tyr Lys Lys Pro Glu
 1               5
```

```
<210> SEQ ID NO 7
<211> LENGTH: 114
<212> TYPE: PRT
<213> ORGANISM: Artificial Sequence
<220> FEATURE:
<223> OTHER INFORMATION: VH region amino acid sequence of hybridoma
      clone C4.8

<400> SEQUENCE: 7
```

```
Glu Val Gln Leu Val Glu Ser Gly Gly Gly Leu Val Gln Pro Gly Glu
 1               5                  10                  15

Ser Leu Lys Leu Ser Cys Glu Ser Asn Glu Tyr Glu Phe Pro Ser His
                20                  25                  30

Asp Met Ser Trp Val Arg Lys Thr Pro Glu Lys Arg Leu Glu Leu Val
            35                  40                  45

Ala Ala Ile Asn Ser Asp Gly Gly Ser Thr Tyr Tyr Pro Asp Thr Met
        50                  55                  60

Glu Arg Arg Phe Ile Ile Ser Arg Asp Asn Thr Lys Lys Thr Leu Tyr
 65                  70                  75                  80

Leu Gln Met Ser Ser Leu Arg Ser Glu Asp Thr Ala Leu Tyr Tyr Cys
                85                  90                  95

Ala Arg Gln Tyr Tyr Arg Gly Gly Gly Gln Gly Thr Thr Leu Thr Val
            100                 105                 110

Ser Ser
```

```
<210> SEQ ID NO 8
<211> LENGTH: 121
<212> TYPE: PRT
<213> ORGANISM: Artificial Sequence
<220> FEATURE:
<223> OTHER INFORMATION: VH region amino acid sequence of hybridoma
      clone C5.5

<400> SEQUENCE: 8
```

```
Glu Val Gln Leu Val Glu Ser Gly Gly Gly Leu Val His Pro Gln Gly
1               5                   10                  15

Ser Leu Lys Leu Ser Cys Thr Ala Ser Gly Phe Thr Phe Asn Thr Tyr
            20                  25                  30

Asp Met Asn Trp Val Arg Gln Ala Pro Gly Lys Gly Leu Glu Trp Val
        35                  40                  45

Ala Arg Ile Arg Thr Lys Ser Tyr Tyr Tyr Ala Thr Tyr Tyr Ala Asp
    50                  55                  60

Ser Val Lys Asp Arg Phe Thr Ile Ser Arg Asp Asp Ser Gln Thr Met
65                  70                  75                  80

Leu Tyr Leu Gln Leu Asn Asn Leu Lys Thr Glu Asp Thr Ala Leu Tyr
                85                  90                  95

Tyr Cys Val Arg Arg Ser Gly Asn Tyr Gly Ala Met Asp Tyr Trp Gly
            100                 105                 110

Gln Gly Thr Ser Val Thr Val Ser Ser
            115                 120

<210> SEQ ID NO 9
<211> LENGTH: 108
<212> TYPE: PRT
<213> ORGANISM: Artificial Sequence
<220> FEATURE:
<223> OTHER INFORMATION: VL region amino acid sequence of hybridoma
      clones C4.8 and C5.5

<400> SEQUENCE: 9

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Arg Thr Phe Gly Gly Gly Thr Lys Leu Glu Ile Lys
            100                 105

<210> SEQ ID NO 10
<211> LENGTH: 4
<212> TYPE: PRT
<213> ORGANISM: Artificial Sequence
<220> FEATURE:
<223> OTHER INFORMATION: Hapten

<400> SEQUENCE: 10

Gln Cys Leu Arg
1

<210> SEQ ID NO 11
<211> LENGTH: 7
<212> TYPE: PRT
<213> ORGANISM: Artificial Sequence
<220> FEATURE:
<223> OTHER INFORMATION: Light chain CDR1

<400> SEQUENCE: 11
```

Ser Ser Val Ser Ser Ser Tyr
1               5

<210> SEQ ID NO 12
<211> LENGTH: 4
<212> TYPE: PRT
<213> ORGANISM: Artificial Sequence
<220> FEATURE:
<223> OTHER INFORMATION: Inhibitor of human leukocyte elastase
<220> FEATURE:
<221> NAME/KEY: MOD_RES
<222> LOCATION: (1)..(1)
<223> OTHER INFORMATION: N-(methoxysuccinyl)-Ala
<220> FEATURE:
<221> NAME/KEY: MOD_RES
<222> LOCATION: (4)..(4)
<223> OTHER INFORMATION: Val-chloromethyl ketone

<400> SEQUENCE: 12

Ala Ala Pro Val
1

<210> SEQ ID NO 13
<211> LENGTH: 9
<212> TYPE: PRT
<213> ORGANISM: Artificial Sequence
<220> FEATURE:
<223> OTHER INFORMATION: Light chain CDR3

<400> SEQUENCE: 13

His Gln Tyr His Arg Ser Pro Arg Thr
1               5

<210> SEQ ID NO 14
<211> LENGTH: 8
<212> TYPE: PRT
<213> ORGANISM: Artificial Sequence
<220> FEATURE:
<223> OTHER INFORMATION: Heavy chain CDR1

<400> SEQUENCE: 14

Glu Tyr Glu Phe Pro Ser His Asp
1               5

<210> SEQ ID NO 15
<211> LENGTH: 8
<212> TYPE: PRT
<213> ORGANISM: Artificial Sequence
<220> FEATURE:
<223> OTHER INFORMATION: Heavy chain CDR2

<400> SEQUENCE: 15

Ile Asn Ser Asp Gly Gly Ser Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Heavy chain CDR3

<400> SEQUENCE: 16

Ala Arg Gln Tyr Tyr Arg Gly
1               5

<210> SEQ ID NO 17
<211> LENGTH: 8

```
<212> TYPE: PRT
<213> ORGANISM: Artificial Sequence
<220> FEATURE:
<223> OTHER INFORMATION: Heavy chain CDR1

<400> SEQUENCE: 17

Gly Phe Thr Phe Asn Thr Tyr Asp
1               5

<210> SEQ ID NO 18
<211> LENGTH: 10
<212> TYPE: PRT
<213> ORGANISM: Artificial Sequence
<220> FEATURE:
<223> OTHER INFORMATION: Light chain CDR2

<400> SEQUENCE: 18

Ile Arg Thr Lys Ser Tyr Tyr Tyr Ala Thr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Light chain CDR3

<400> SEQUENCE: 19

Val Arg Arg Ser Gly Asn Tyr Gly Ala Met Asp Tyr
1               5                   10

<210> SEQ ID NO 20
<211> LENGTH: 4
<212> TYPE: PRT
<213> ORGANISM: Artificial Sequence
<220> FEATURE:
<223> OTHER INFORMATION: Substrate for human leukocyte elastase
<220> FEATURE:
<221> NAME/KEY: MOD_RES
<222> LOCATION: (1)..(1)
<220> FEATURE:
<221> NAME/KEY: MOD_RES
<222> LOCATION: (4)..(4)
<223> OTHER INFORMATION: Val-amino-4-methylcoumarin

<400> SEQUENCE: 20

Ala Ala Pro Val
1
```